United States Patent [19]

Hudz

[11] Patent Number: 5,496,356
[45] Date of Patent: Mar. 5, 1996

[54] PIEZO DE-TOXIFIER

[76] Inventor: Paul H. Hudz, 3400 Inverness St., Redding, Calif. 96002

[21] Appl. No.: 341,268

[22] Filed: Nov. 16, 1994

Related U.S. Application Data

[63] Continuation of Ser. No. 38,789, Mar. 29, 1993, abandoned.

[51] Int. Cl.⁶ .................................................. A61N 1/32
[52] U.S. Cl. ........................ 607/72; 607/115; 607/145; 607/148; 361/232; 273/84 ES
[58] Field of Search ........................... 607/72, 145, 115, 607/148–150; 273/84 ES; 310/319, 339; 361/232

[56] References Cited

U.S. PATENT DOCUMENTS

| | | |
|---|---|---|
| 3,457,461 | 7/1969 | Steinke et al. . |
| 3,564,341 | 2/1971 | Nichiura . |
| 3,758,827 | 9/1973 | Schroder et al... |
| 3,826,952 | 7/1974 | Iwasaki et al. . |
| 3,829,737 | 8/1974 | Johnson . |
| 4,297,609 | 10/1981 | Hirao et al. ............................. 310/339 |
| 4,315,180 | 2/1982 | Kondo et al. ............................. 310/339 |
| 4,741,347 | 3/1988 | Robert et al. ............................. 607/150 |
| 4,873,609 | 10/1989 | Mackey ................................. 273/84 ES |
| 5,074,305 | 12/1991 | Guderian ............................... 607/72 X |
| 5,235,990 | 8/1993 | Dempsey ................................. 607/145 |

FOREIGN PATENT DOCUMENTS

| | | | |
|---|---|---|---|
| 1448644 | 9/1976 | United Kingdom | 607/145 |
| 8505042 | 11/1985 | WIPO | 607/115 |
| 8704068 | 7/1987 | WIPO | 607/145 |

*Primary Examiner*—William E. Kamm
*Assistant Examiner*—Jeffrey R. Jastrzab
*Attorney, Agent, or Firm*—John J. Leavitt

[57] ABSTRACT

A pen size apparatus for neutralizing and detoxifying bites and stings to man or animal from insects and reptiles. When the apparatus is positioned on the affected area of the toxin victim and a push-button is depressed, multiple piezo crystals are stressed producing low amperage direct current high voltage pulses. The apparatus produces these pulses every time the push-button is depressed without any other internal or external power source. These pulses are transmitted through appropriate electrodes in contact with the affected area of the toxin victim, where detoxification takes place by electrolysis, anaphoresis, and cataphoresis.

8 Claims, 5 Drawing Sheets

PIEZO DE-TOXIFIER

This is a continuation of application Ser. No. 08/038,789 filed on Mar. 29, 1993, now abandoned.

DESCRIPTION OF THE PRIOR ART

There has been a need for a personal detoxifier for the outdoors person or anyone that is exposed to toxic bites (for example, insect bites, bee stings, scorpion bites, etc.) as a first aid measure. Many times these bites and stings result in the injection of substances that are toxic to the person, resulting in an immediate burning sensation and swelling. The more severe reactions could, however, vary from nausea and vomiting, abdominal pain, respiratory difficulty and death.

First Aid Treatment may vary depending on the bite or sting. The first objective of treatment is to immobilize the affected member. A tourniquet may be applied proximal to the wound (only tight enough to impede venous and lymphatic drainage), as well as cold compacts. The person then is taken to medical treatment facilities.

Reports on the effects of radiation on venoms are somewhat conflicting. Jackson (1927, p. 204) stated that X rays reduced toxicity. Welch (1930, p. 37) found that although cold and light had little effect on dried venom, radium enemations destroyed its toxicity and its antigenic quality as well. He found that it was also detoxified by ultraviolet light. Macht (1935, p. 520), on the other hand, stated that X-rays and radium were without effect, but that ultraviolet light reduced toxicity. Davenport (1943, p. 25) says that dried venom deteriorates in the light (see also Boquet, 1948, p. 82). Welch (1930, p. 37) records electricity as being destructive of dry venom.

FIELD OF THE INVENTION

Electro-detoxification

The perfect Detoxifier should be constructed so that it completely breaks down toxic compounds, is small and could be carried on ones person.

The perfect Detoxifier is difficult to achieve because of the following:

1. The multiplicity of toxic organic compounds involved.
2. The availability of the detoxification equipment.
3. The operability and utility of the apparatus. (It should be possible to use the Detoxifier in treating oneself.)
4. The possibility that it becomes inoperative because of dead batteries or lack of adequate power source.

It has been shown that the application of low amperage direct current high voltage pulses to the local area results in the breaking down of the toxic compounds by means of electrolysis. It is also interesting to note that anaphoresis and cataphoresis is taking place.

The bite site is the in situ electrolysis cell. The skin, blood and intracellular fluid is the electrolyte. The electrodes placed on the surface of the skin are the electrodes of the in situ electrolysis cell. The Piezo De-Toxifier produces low amperage direct current high voltage pulses and delivers these pulses to the contact electrodes.

The normal ionic content of blood plasma and intracellular fluid of muscle cells are thus listed.

| | |
|---|---|
| $Na^+$ | $HCO_3^-$ |
| $K^+$ | $HPO_4^{2-}$ |
| $Ca^{+2}$ | Protein |
| $Mg^{+2}$ | |

The current that flows when a given voltage is applied depends primarily on the concentration of the solution, the size of the electrodes, and the distance between the electrodes. The intruding toxic compounds from the sting or bite are broken down to their simple elemental form. These simple elemental forms usually are not toxic to the person.

BACKGROUND OF THE INVENTION

The Piezo De-Toxifier provides a series of low amperage direct current high voltage pulses that may be used for a wide range of bites and stings inflicted on humans and animals. The treatment is harmless although the momentary "pricks" felt at each pulse may be annoying.

The treatment results in the alleviation and detoxification of the following:

a. Stings from bees, wasps, scorpions, sting rays, etc.
b. Bites from mosquitoes, ants, spiders, and snakes.
c. Itching from any of the above lesions, plus ring worms, lice, chiggers, jiggers, fleas, bluebottle flies, etc.

The beneficial effects of administering immediate detoxification to the area of a bite or stings are, of course, the immediate reduction in toxicity. The results are the reduction of swelling, burning sensation, and other side effects. It has been observed that even when the area is treated after the swelling has started, that the swelling immediately begins subsiding. The burning sensation also subsides.

DISCLOSURE OF THE INVENTION

The Piezo De-Toxifier is constructed using proven piezo-electric ceramic crystals and appropriate mechanical means for producing high voltage direct current pulses. The resulting Piezo De-Toxifier is extremely small. It may be carried on the person in a pocket or pack, making it readily available should the need arise. The mechanical mechanism that is used makes it foolproof and easy to operate. The Piezo De-Toxifier never requires replacement of batteries or recharging of the same. The major components of the Piezo De-Toxifier are the two piezo-electric ceramic disks, which transform mechanical energy to high voltage direct current pulses.

The Piezo De-Toxifier has a mechanical means for producing low amperage direct current high voltage pulses to detoxify toxic substances injected into the body through bites and stings. The mechanical means transform the physical action of pushing a button, to low amperage direct current high voltage pulses. Each such action produces low amperage direct current high voltage pulses.

The injected toxins are detoxified by electrolysis means, anaphoresis means and cataphoresis means. The toxins and body fluids become the electrolyte and the piezo-electric Detoxifier is the portable power source. The Piezo De-Toxifier electrode rings are the electrodes of the in situ electrolysis cell. The toxic compounds are dissociated through electrolysis, anaphoresis and cataphoresis into their elemental forms, which are usually not toxic to the biosystem; therefore, the body is capable of expelling them.

The mechanical stress on each of the piezo-ceramic crystals generates low amperage direct current high voltage pulses which are conducted to the external electrode rings of the Piezo De-Toxifier.

The Piezo De-Toxifier is activated by placing the Piezo De-Toxifier upon the skin at the site of the sting or bite and depressing the push-button. The action of the initial force on the push-button begins compressing the main energy spring. Pushing the push-button still further stores more energy in the main energy spring until finally the hammer is pushed off the ledge. This releases all of the energy stored in the main energy spring, propelling the hammer with all of the energy stored in the main energy spring against the reset spring and punch. The punch transmits the shock wave to the first piezo crystal, through the piezo inter crystal spacer, to the second piezo crystal and finally, the remaining mechanical shock is absorbed by the inertia anvil and anvil spacers. The mechanical energy is mainly absorbed by the first and second piezo crystals, and is translated into low amperage direct current high voltage pulses. Upon release of the push button of the Piezo De-Toxifier the reset spring pushes the hammer and energy spring back up until the hammer lodges on the inner ledge of the Piezo De-Toxifier housing. This action resets the mechanism for the next cycle.

PREFERRED EMBODIMENT

Figure 1:
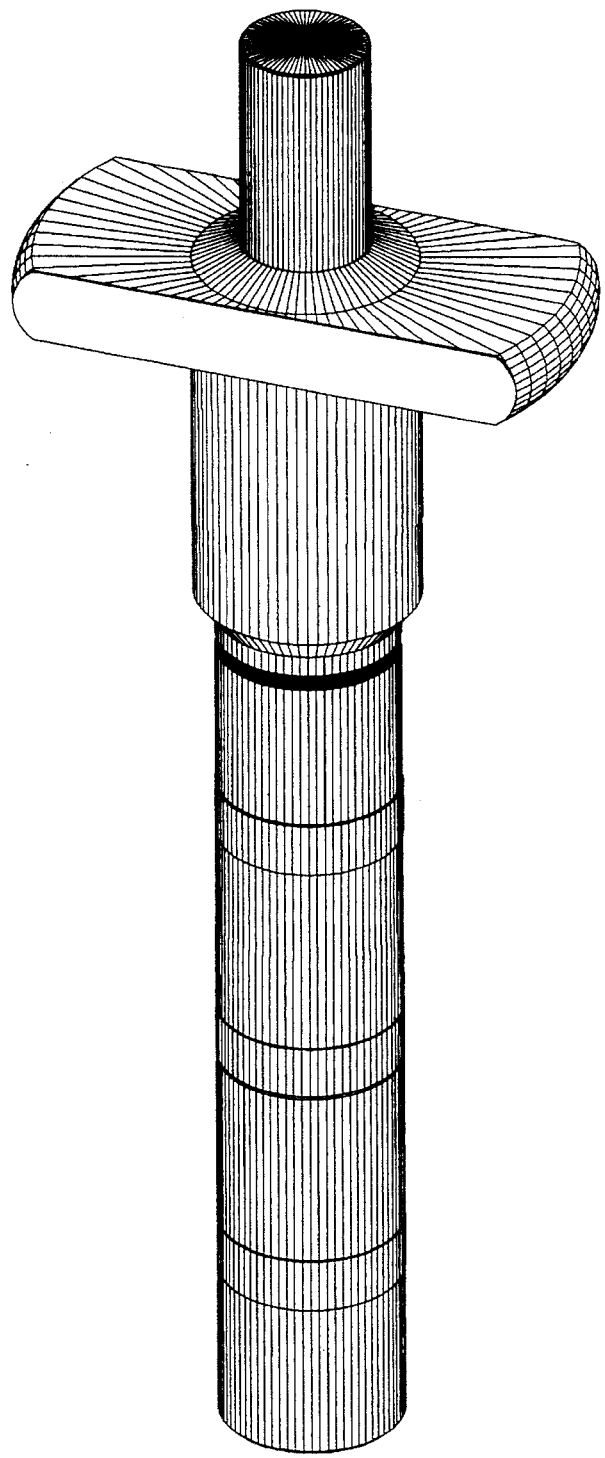
FIG. 1. is a perspective view of the Piezo De-Toxifier (with housing cover removed)
Figure 2:
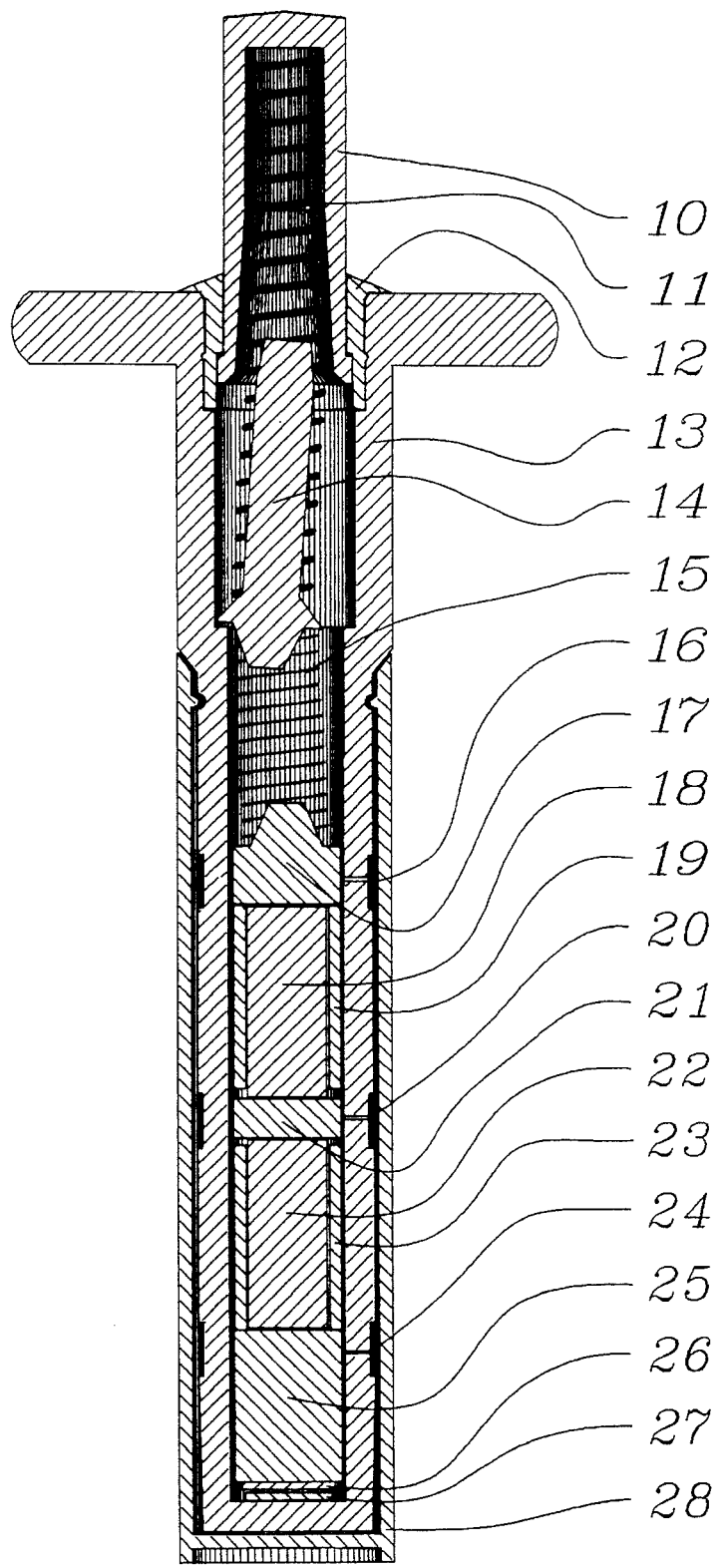
FIG. 2. is a cross-section, side elevation of the Piezo De-Toxifier with the push-button at rest ready for operation.
Figure 3:
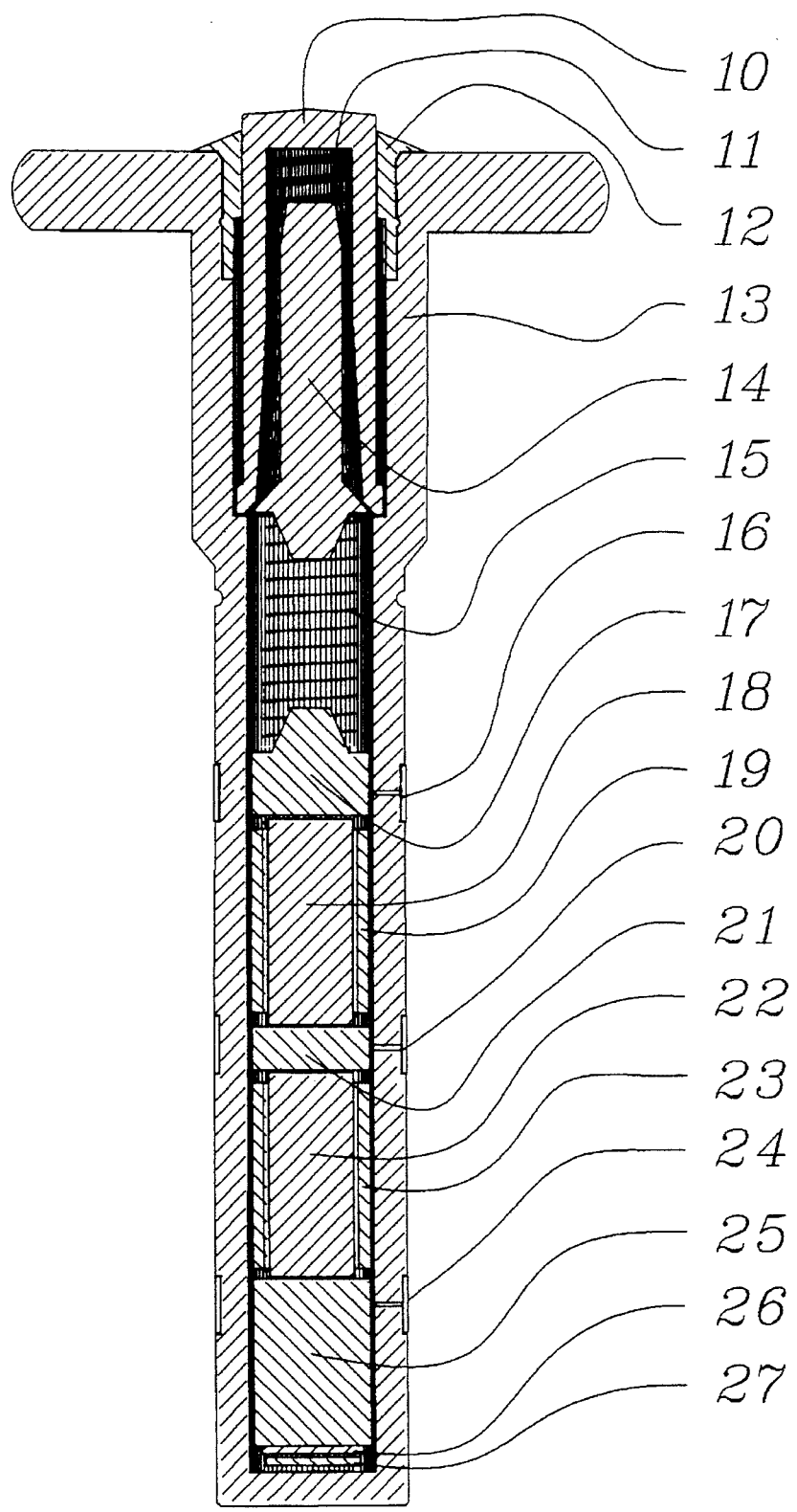
FIG. 3. is a cross-section, side elevation of the Piezo De-Toxifier with the push-button fully depressed at the moment of releasing of the compression spring.
Figure 4:
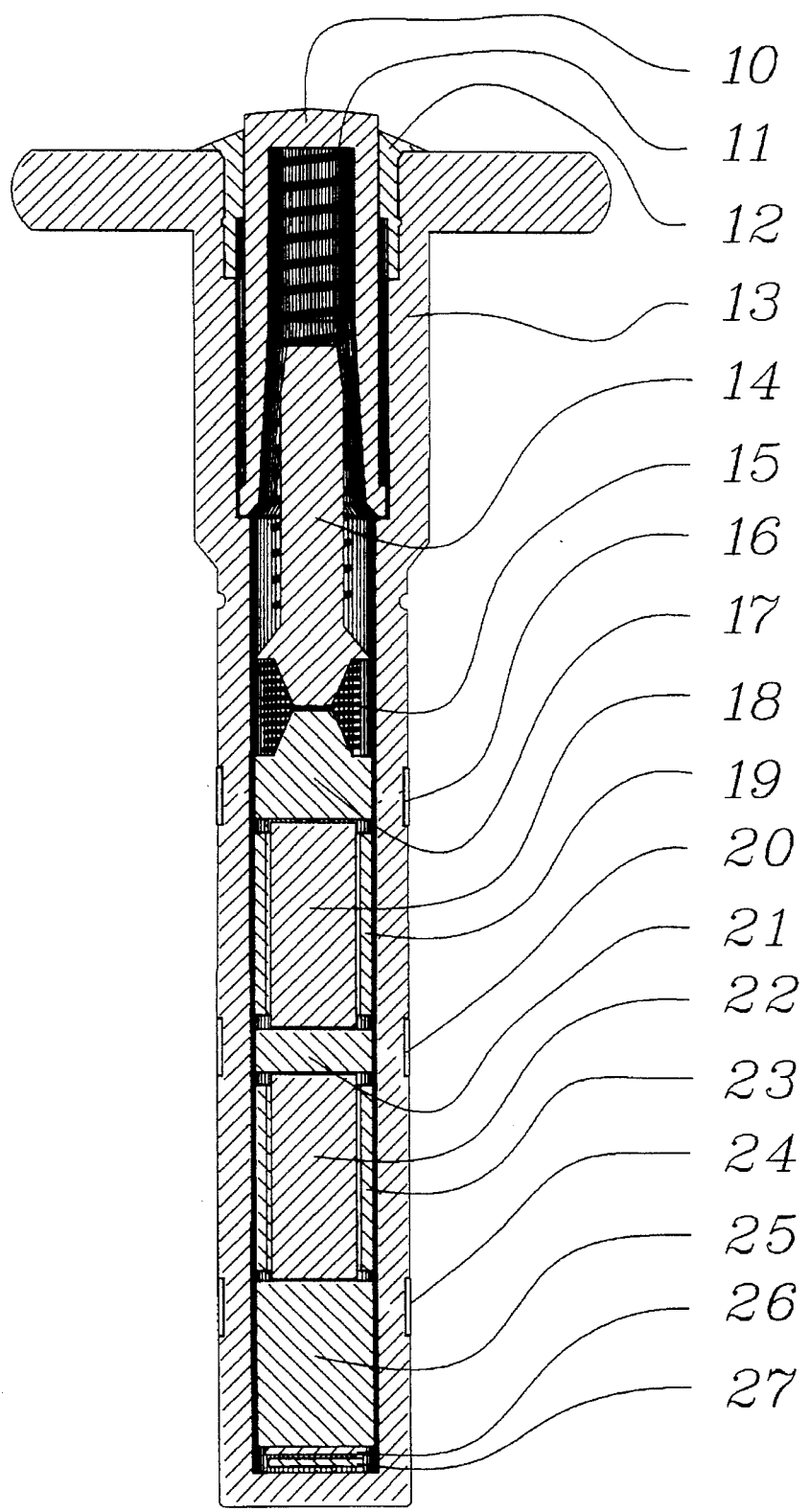
FIG. 4. is a cross-section, side elevation of the Piezo De-Toxifier with the hammer at the moment of impact upon the punch.
Figure 5:
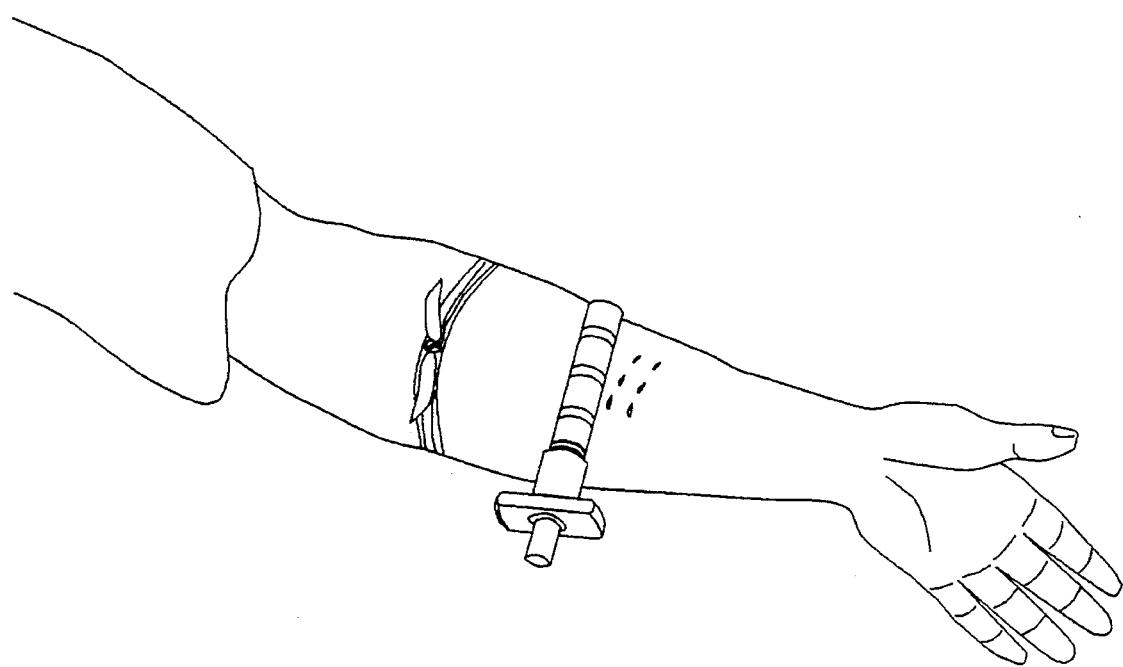
FIG. 5. is a perspective view of the Piezo De-Toxifier being used on a limb.

The Piezo De-Toxifier is positioned on the area of the bite in such a way as to have the electrodes(16),(20),(24) in contact with the skin, then the push-button (10) is depressed. This action causes the compression of the main energy spring(11), until the push-button(10) reaches the limit of its travel, and the hammer is pushed off of the internal ledge of the housing(13).

Whereupon the compressed main energy spring(11) releases its energy propelling the hammer(14) toward the punch(17). The hammer(14) begins compressing the light tension reset spring(15) then impacts the punch(17) which is in intimate contact with the face of the first piezo crystal(18).

This impact stresses the first piezo crystal(18), and passes some of the mechanical shock wave on to the intercrystal spacer(21). The first piezo crystal insulator(19) serves to insulate the first piezo crystal(18).

This shock wave passes through the intercrystal spacer(21) and mechanical stresses the second piezo crystal(22) which is backed by the inertia absorbing anvil(25). The second piezo crystal insulator (22) serves to insulate the second piezo crystal(23).

Upon the release of the push button(10), the fully compressed reset spring(15), pushes the hammer(14) back to latch on the internal ledge of the housing(13). The Piezo De-Toxifier is now ready for the next action cycle.

DESCRIPTION OF THE PREFERRED EMBODIMENT

Referring in detail to the accompanying drawings. The push-button(10) is retained in the housing(13) by the push-button retainer(12). This retains all the parts that are assembled within the body(13) from the bottom to the top as follows: second anvil spacer(27), first anvil spacer(26), inertia anvil(25), second piezo crystal insulator(23),second piezo crystal(22), piezo inter crystal spacer(21), first piezo crystal insulator(19), first piezo crystal(18), punch(17), reset spring(15), hammer(14), and main energy spring(11).

The housing(13) of the Piezo De-Toxifier is placed on the area of the bite or sting, preferably with all three electrodes(16,20,24) in intimate contact with the skin. The pushbutton(10) is depressed until it reaches the end of its travel. The beginning of this action begins the compression of the main energy spring(11); as the action continues, the spring is further compressed until the pushbutton(10) reaches the end of its travel, whereupon it centers the hammer(14) which slides off of the inner ledge of the housing(13).

The compressed main energy spring then propels the hammer(14) and begins compressing the light reset spring(15); the hammer ultimately impacts the punch (17).

The punch(17) transmits sequentially the mechanical shock wave to the first piezo crystal(18), the inter crystal spacer(21), the second piezo crystal(22), and the inertia anvil(25).

The mechanical shock wave passes through the first piezo crystal(18), producing a low ampere current high voltage pulse which flows to the electrode (16) through insitu electrolysis cell(skin, blood and intercellular fluid) to electrode(20).

Part of the mechanical shock wave travels on through the inter crystal spacer(21) and mechanically stresses the second piezo crystal(23), producing a low ampere current high voltage pulse which flows to the electrode (20), then through the insitu electrolysis cell(skin blood and intercellular fluid) to the electrode(24).

The remainder of the mechanical shock is absorbed by the inertia anvil(25), the spacer(26), and the spacer(27).

The invention has been described in detail with particular reference to a preferred embodiment thereof, but it will be understood that variations and modifications can be effected within the spirit and scope of this invention.

What is claimed is:

1. An apparatus adapted to be hand-held and selectively operable to generate an electric current of high voltage and low amperage and manipulable to conduct said electric current through live tissue containing insect or reptile toxins, for the purpose of electro detoxifying said toxins, said apparatus comprising:

a) a hollow electrically non-conductive housing;

b) at least one piezoelectric member enclosed within said electrically non-conductive housing;

c) means for stressing said at least one piezoelectric member mounted on said housing and selectively operable to generate a low amperage electric current to effect said stressing; and d) at least one electrode of electrically conductive material mounted exteriorly on said hollow housing adapted for conductive contact with live tissue and adapted to conduct a low amperage electrical current from said piezoelectric member through said live tissue to electro detoxify toxins contained in said live tissue;

e) said means mounted on said housing for stressing said at least one piezoelectric member including a push-button slidably mounted on one end of the hollow housing and positioned for easy application of an axially directed force thereto by digital manipulation to drive said push-button into said hollow housing, a push-button retainer fixedly mounted on said housing for retaining said push-button, said means mounted on said housing operable to stress said piezoelectric member, and said piezoelectric member within said hollow housing.

2. The apparatus of claim 1, wherein said means mounted on said housing operable to stress said at least one piezoelectric member includes a main energy compression spring one end portion of which resiliently impinges on said push-button and which upon compression by slidable displacement of said push-button stores sufficient energy to stress said piezoelectric member, and a hammer within the hollow housing impinged by the end of said main energy compression spring remote from said push-button to transfer the stored energy from said main energy compression spring to drive said hammer to stress said piezoelectric member and thereby generate said low amperage electric current.

3. The apparatus of claim 2, wherein a punch of rigid electrical conducting material is disposed in said housing between said hammer and said piezoelectric member, and a reset compression spring is provided within the housing disposed between said punch and said hammer to retract said hammer, said main energy compression spring, and said push-button upon removal of said axially directed outside force imposed on said push-button.

4. The apparatus of claim 3, wherein said at least one electrode comprises a ring encompassing said hollow housing and making electrical contact with said punch, said ring electrode being of suitable width whereby sufficient electrical contact area is provided for electrically conductive skin contact on said live tissue.

5. The apparatus of claim 4, wherein said hollow housing is provided with a closed end remote from said push-button, and an inertia anvil is provided interposed between said closed end of the housing and the at least one piezoelectric member, said anvil being of sufficient mass to provide sufficient inertia whereby said at least one piezoelectric member is operably stressed.

6. The apparatus of claim 5, wherein at least three electrodes of conducting material are exteriorly mounted spaced along said hollow housing and in electrical contact with said inertia anvil, said third electrode being of suitable width whereby sufficient electrical contact is provided for electrically conductive skin contact on said live tissue.

7. An apparatus adapted to be hand-held and selectively operable to generate an electric current of high voltage and low amperage and manipulable to conduct said electric current through live tissue containing insect or reptile toxins, for the purpose of electro detoxifying said toxins, said apparatus comprising:

a) a hollow electrically non-conductive housing;

b) at least one piezoelectric member enclosed within said electrically non-conductive housing;

c) means for stressing said at least one piezoelectric member mounted on said housing and selectively operable to generate a low amperage electric current to effect said stressing; and d) at least one electrode of electrically conductive material mounted exteriorly on said hollow housing adapted for conductive contact with live tissue and adapted to conduct a low amperage electrical current from said piezoelectric member through said live tissue to electro detoxify toxins contained in said live tissue;

e) wherein at least two axially spaced piezoelectric members are provided within the housing, and a spacer of rigid electrical conducting material is provided between said piezoelectric members whereby said spacer transfers mechanically generated stress from one piezoelectric member to the other piezoelectric member.

8. The apparatus of claim 7, wherein a second electrode of electrically conducting material encompasses said hollow housing and is in electrical contact with said spacer, said second electrode being of suitable width whereby sufficient electrical contact is provided for electrically conductive skin contact on said live tissue.

* * * * *